United States Patent
Leem et al.

(10) Patent No.: US 9,612,212 B1
(45) Date of Patent: Apr. 4, 2017

(54) ELLIPSOMETER AND METHOD OF INSPECTING PATTERN ASYMMETRY USING THE SAME

(71) Applicant: Samsung Electronics Co., Ltd., Suwon-si (KR)

(72) Inventors: Choonshik Leem, Seoul (KR); Chungsam Jun, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/954,158

(22) Filed: Nov. 30, 2015

(51) Int. Cl.
| | |
|---|---|
| *G01N 21/00* | (2006.01) |
| *G01N 21/956* | (2006.01) |
| *G01N 21/21* | (2006.01) |
| *G01N 21/88* | (2006.01) |
| *H01L 21/66* | (2006.01) |
| *H01L 21/768* | (2006.01) |

(52) U.S. Cl.
CPC ......... *G01N 21/956* (2013.01); *G01N 21/211* (2013.01); *G01N 21/8806* (2013.01); *H01L 21/76816* (2013.01); *H01L 21/76877* (2013.01); *H01L 22/12* (2013.01); *G01N 2021/8848* (2013.01)

(58) Field of Classification Search
CPC .............. G01N 21/956; G01N 21/211; G01N 21/8806; H01L 22/12; H01L 21/76816; H01L 21/76877
See application file for complete search history.

(56) References Cited

U.S. PATENT DOCUMENTS

| | | | |
|---|---|---|---|
| 6,104,486 A | 8/2000 | Arimoto | |
| 6,441,398 B2 | 8/2002 | Yang et al. | |
| 6,937,333 B2 | 8/2005 | Horie et al. | |
| 7,095,498 B2 | 8/2006 | Horie | |
| 7,277,172 B2 | 10/2007 | Kandel et al. | |
| 8,446,578 B2 | 5/2013 | Sugihara et al. | |
| 2005/0088665 A1* | 4/2005 | Bischoff | G01N 21/956 356/601 |
| 2006/0274310 A1* | 12/2006 | Kandel | G01N 21/211 356/369 |

(Continued)

FOREIGN PATENT DOCUMENTS

| | | |
|---|---|---|
| JP | 2002-176085 | 6/2002 |
| JP | 2007-309874 | 11/2007 |

(Continued)

*Primary Examiner* — Richard Booth
(74) *Attorney, Agent, or Firm* — H.C. Park & Associates, PLC

(57) ABSTRACT

An ellipsometer includes a stage, a light source, a polarizer, a detector, and a processor. The stage is configured to support a substrate including a pattern. The light source is configured to emit illumination toward the substrate. The polarizer is configured to polarize the illumination. The detector is configured to generate, in association with a plurality of azimuthal angles, data corresponding to polarized illumination reflected from the substrate. The processor is configured to: control rotation of the stage in association with sequential inspection of the pattern at the plurality of azimuthal angles, and determine asymmetry of the pattern based on the data. Each azimuthal angle of the plurality of azimuthal angles corresponds to a different rotational state of the stage.

12 Claims, 7 Drawing Sheets

(56) References Cited

U.S. PATENT DOCUMENTS

2013/0033704 A1* 2/2013 Zhuang .............. G01N 21/4785
                                                              356/138
2015/0009504 A1   1/2015 Finarov et al.

FOREIGN PATENT DOCUMENTS

| JP | 2011-007626 | 1/2011 |
| JP | 2011-141285 | 7/2011 |
| JP | 2013-002900 | 1/2013 |
| JP | 2014-006236 | 1/2014 |

* cited by examiner

ELLIPSOMETER AND METHOD OF INSPECTING PATTERN ASYMMETRY USING THE SAME

BACKGROUND

Field

Exemplary embodiments relate to a semiconductor inspection device and a method of inspecting a semiconductor pattern using the same, and, more particularly, to a semiconductor inspection device configured to measure a profile of a semiconductor pattern and a method of measuring a profile of a semiconductor pattern using the same.

Discussion

High performance semiconductors are used in various electronic devices. An aspect of designing a high performance semiconductor device may include scaling down the size of a semiconductor device so that more semiconductor devices may be formed on a single wafer (or substrate). As a way of increasing a degree of integration of a semiconductor device, a vertically structured semiconductor device, such as V-NAND, may be utilized to reduce the size (or footprint) of the semiconductor device, while increasing the number of formed cells.

Fabricating highly integrated semiconductor devices, such as vertically structured semiconductor devices, may involve forming various patterns in a semiconductor device, such as holes, to electrically and/or physically connect elements patterned across multiple layers. For example, symmetrically formed holes may be formed in a semiconductor structure to generally improve the electrical characteristics of a semiconductor device. However, during the semiconductor fabrication process, semiconductor patterns, such as holes, may be formed asymmetrically. As such, the patterns may be misaligned with other components or a planar surface of a substrate. This may degrade electrical characteristics of the semiconductor device.

Non-destructive inspection devices may be used to identify a semiconductor pattern having asymmetrical orientation. Non-destructive inspection devices may include a spectroscopic ellipsometer. A spectroscopic ellipsometer may measure optical properties of a target by emitting a polarized beam towards the target and detecting scattered or reflected signals from the target. In this manner, the spectroscopic ellipsometer may collect the detected signals and calculate a 4×4 matrix (or Mueller matrix) to generate an optical profile (e.g., polarimetric properties) of the target. Generally, in semiconductor fabrication, the target may include a semiconductor device and the optical profile may include asymmetry of a semiconductor pattern in the semiconductor device.

Mueller matrix components, such as (1,3), (1,4), (2,3), and (2,4) components, may be used to identify asymmetry in the target. For instance, a spectroscopic ellipsometer utilizing a Mueller matrix may measure an asymmetry of the target by predetermining an inclined direction of a semiconductor pattern formed therein. The predetermined inclined direction may be a presumed value because the inclined direction of a semiconductor pattern, such as a hole, may not be externally observable. When the predetermined direction of the semiconductor pattern does not correspond to an actual inclined direction of the semiconductor pattern, depending on an azimuthal angle of the polarized beam incident to the target, the Muller matrix components representing the asymmetry may be zero (0). This may indicate a symmetrical orientation even though the holes may be inclined. Given that the output of a conventional spectroscopic ellipsometer may rely on the presumed orientation of the semiconductor pattern, it is difficult to generate a correct profile of a semiconductor pattern.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide a semiconductor inspection device configured to measure a profile of a semiconductor device and a method of measuring a profile of a semiconductor device using the same.

Additional aspects will be set forth in the detailed description which follows, and, in part, will be apparent from the disclosure, or may be learned by practice of the inventive concept.

According to one or more exemplary embodiments, an ellipsometer includes a stage, a light source, a polarizer, a detector, and a processor. The stage is configured to support a substrate including a pattern. The light source is configured to emit illumination toward the substrate. The polarizer is configured to polarize the illumination. The detector is configured to generate, in association with a plurality of azimuthal angles, data corresponding to polarized illumination reflected from the substrate. The processor is configured to: control rotation of the stage in association with sequential inspection of the pattern at the plurality of azimuthal angles, and determine asymmetry of the pattern based on the data. Each azimuthal angle of the plurality of azimuthal angles corresponds to a different rotational state of the stage.

According to one or more exemplary embodiments, a method includes: causing, at least in part, a substrate to be rotated to a plurality of azimuthal orientations, the substrate including a pattern; causing, at least in part, polarized illumination to propagate towards the substrate; causing, at least in part, polarized illumination reflected from the substrate to be detected; generating, in association with each azimuthal orientation of the plurality of azimuthal orientations, data corresponding to the detected polarized illumination; and determining asymmetry of the pattern based on the data.

According to one or more exemplary embodiments, a method of manufacturing a semiconductor device includes: forming the pattern on a substrate; loading the substrate on a stage; rotating the substrate to a plurality of azimuthal orientations; irradiating polarized illumination towards the substrate; detecting polarized illumination reflected from the substrate; generating, in association with each azimuthal orientation of the plurality of azimuthal orientations, data corresponding to the detected polarized illumination; and determining asymmetry of the pattern based on the data.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION OF THE ILLUSTRATED EMBODIMENTS

Figure 1:
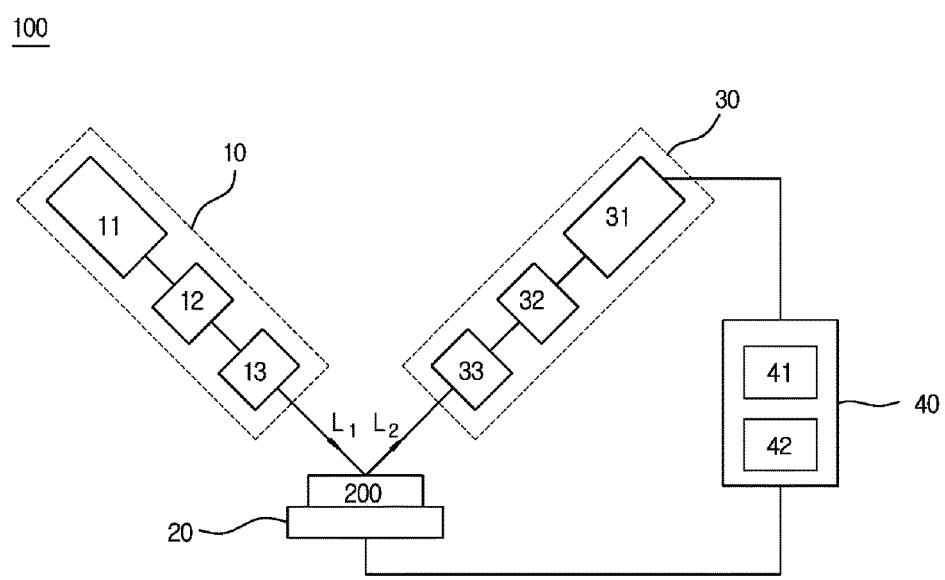
FIG. 1 is a block diagram of a semiconductor inspection device, according to one or more exemplary embodiments.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes components, etc., may be exaggerated for clarity and descriptive purposes. Also, like reference numerals denote like elements.

When an element or component is referred to as being "on," "connected to," or "coupled to" another element, it may be directly on, connected to, or coupled to the other element or intervening elements may be present. When, however, an element or component is referred to as being "directly on," "directly connected to," or "directly coupled to" another element or component, there are no intervening elements or components present. For the purposes of this disclosure, "at least one of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, and/or sections, these elements, components, and/or sections should not be limited by these terms. These terms are used to distinguish one element, component, and/or section from another element, component, and/or section. Thus, a first element, component, and/or section discussed below could be termed a second element, component, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

FIG. 1 is a block diagram of a semiconductor inspection device, according to one or more exemplary embodiments.

Referring to FIG. 1, inspection device 100 may be a non-destructive inspection device configured to measure various properties of a target, such as asymmetry, thickness, refractive index, uniformity, and surface roughness, by emitting one or more polarized beams towards the target and detecting a change of intensity and/or phase of one or more reflected and/or scattered beams from the target. Inspection device 100 may include a spectroscopic ellipsometer to non-destructively analyze the configuration of a semiconductor, such as the configuration of a semiconductor pattern. Accordingly, for descriptive convenience, inspection device 100 will be referred to, hereinafter, as semiconductor inspection device 100. It is contemplated, however, that inspection device 100 may be utilized in association with any suitable metrological implementation.

According to one or more exemplary embodiments, semiconductor inspection device 100 may be utilized to analyze the configuration of sample wafer 200 including a semiconductor pattern. Semiconductor inspection device 100 may include emitter 10 configured to emit one or more optical beams $L_1$ towards sample wafer 200, and collector 30 configured to collect reflected, refracted, transmitted, scattered, etc., optical beam(s) $L_2$ from sample wafer 200. Semiconductor inspection device 100 may further include stage 20. Sample wafer 200 may be mounted (or otherwise supported) on stage 20. Processor 40 may be utilized to control a movement of semiconductor inspection device 100 (e.g., movement of stage 20), as well as to generate a profile of a semiconductor pattern based on data collected via collector 30. In this manner, processor 40 may be utilized to control a semiconductor inspection process, as will be described in more detail in association with FIG. 5.

Emitter 10 may include light source 11 to emit an optical beam, which may be (or include) parallel rays, polarizer 12 to polarize the optical beam into a polarized beam (e.g., a linearly polarized beam), and first compensator 13 to adjust or retard a phase of the polarized beam to emit polarized beam $L_1$.

Collector 30 may include second compensator 33 to modify a polarization state of reflected beam $L_2$ (e.g., adjust or retard a phase of reflected beam $L_2$), which may be reflected, refracted, transmitted, scattered, etc., after polarized beam $L_1$ passes through the semiconductor pattern of sample wafer 200, in a ratio different from a ratio of first compensator 13. For descriptive convenience, beam $L_2$ will be referred to, hereinafter, as reflected beam $L_2$, which may be an elliptically polarized beam. Collector 30 may further include analyzer 32 to analyze data, such as wavelength, polarization, etc., of reflected beam $L_2$, and detector 31 to measure intensity (or amount) of reflected beam $L_2$ incident thereto. The analyzer 32 may be configured to determine orthogonal components of the polarization of reflected beam $L_2$. Detector 31 may receive analyzed reflected beam $L_2$, to generate charges corresponding to the intensity (or amount) of received reflected beam $L_2$, and output the charges to processor 40. Detector 31 may include a two dimensional area image sensor, such as a complementary metal-oxide-semiconductor (CMOS) or a charge coupled device (CCD).

A conventional ellipsometer may utilize a dual-rotating-element ellipsometer, in which two optical elements spin at the same rotating speed and with the same speed ratio. In particular, a combination of polarizer and analyzer, compensator and analyzer, or polarizer and compensator may be the two rotating optical elements. According to one or more exemplary embodiments, emitter 10 and collector 30 may be configured as a dual-rotating-element ellipsometer, but exemplary embodiments are not limited thereto.

Sample wafer 200 may be mounted (or otherwise supported) on stage 20. Stage 20 may rotate in a clockwise or counterclockwise direction. In this manner, polarized beam $L_1$ may be incident with sample wafer 200 to enable inspection in any direction or in a selective range of rotating angles. A rotating interval of stage 20 may be determined according to an inspection environment. Stage 20 may include one or more actuators to effectuate rotation of sample wafer 200, such as continuous, stepwise, variable, etc., rotation of sample wafer 200.

Processor 40 may include operator 41 to calculate properties associated with a semiconductor pattern formed on sample wafer 200, such as to calculate an asymmetry of holes in the semiconductor pattern. Operator 41 may analyze information, such as wavelength, intensity, etc., of reflected beam $L_2$ detected via collector 30. Processor 40 may further include controller 42 to control stage 20 to rotate from a reference position to a first azimuthal angle and from the first azimuthal angle to a second azimuthal angle upon completion of measuring sample wafer 200 at each azimuthal angle. Herein, an azimuthal angle may refer a relative position of sample wafer 200 with respect to a reference position (e.g., an azimuthal angle of 0 degrees) at which polarized beam $L_1$ may be incident. As such, an azimuthal angle may correspond to a direction of sample wafer 200 with respect to the reference position.

According to one or more exemplary embodiments, components of semiconductor inspection device 100, such as polarizer 12, first compensator 13, second compensator 33, and analyzer 32, may rotate (e.g., spin) in a fixed position, such that a waveform of reflected beam $L_2$ may be analyzed by detecting intensity of reflected beam $L_2$ (which may change periodically) via detector 31. The intensity of reflected beam $L_2$ may be calculated (or otherwise determined) utilizing Mueller matrix components, which may correspond to an asymmetry of a semiconductor pattern, through a Fourier coefficient method. For instance, one or more of (1,3), (1,4), (2,3), and (2,4) components of a 4×4 Mueller matrix may correspond to an asymmetry of a semiconductor pattern. For descriptive convenience, the (1,3), (1,4), (2,3), and (2,4) components of the 4×4 Mueller matrix will be referred to, hereinafter, as first, second, third, and fourth elements, respectively.

Processor 40 and/or one or more components thereof, may be implemented via one or more general purpose and/or special purpose components, such as one or more discrete circuits, digital signal processing chips, integrated circuits, application specific integrated circuits, microprocessors, processors, programmable arrays, field programmable arrays, instruction set processors, and/or the like. In this manner, the features, functions, processes, etc., described herein may be implemented via software, hardware (e.g., general processor, digital signal processing (DSP) chip, an application specific integrated circuit (ASIC), field programmable gate arrays (FPGAs), etc.), firmware, or a combination thereof. As such, processor 40 and/or one or more components thereof may include or otherwise be associated with one or more memories (not shown) including code (e.g., instructions) configured to cause processor 40 and/or one or more components thereof to perform one or more of the features, functions, processes, etc., described herein.

The memories may be any medium that participates in providing code to the one or more software, hardware, and/or firmware components for execution. Such memories may be implemented in any suitable form, including, but not limited to, non-volatile media, volatile media, and transmission media. Non-volatile media include, for example, optical or magnetic disks. Volatile media include dynamic memory. Transmission media include coaxial cables, copper wire and fiber optics. Transmission media can also take the form of acoustic, optical, or electromagnetic waves. Common forms of computer-readable media include, for example, a floppy disk, a flexible disk, hard disk, magnetic tape, any other magnetic medium, a compact disk-read only memory (CD-ROM), a rewriteable compact disk (CDRW), a digital video disk (DVD), a rewriteable DVD (DVD-RW), any other optical medium, punch cards, paper tape, optical mark sheets, any other physical medium with patterns of holes or other optically recognizable indicia, a random-access memory (RAM), a programmable read only memory (PROM), and erasable programmable read only memory (EPROM), a FLASH-EPROM, any other memory chip or cartridge, a carrier wave, or any other medium from which information may be read by, for example, a controller/processor.

Figure 2A:
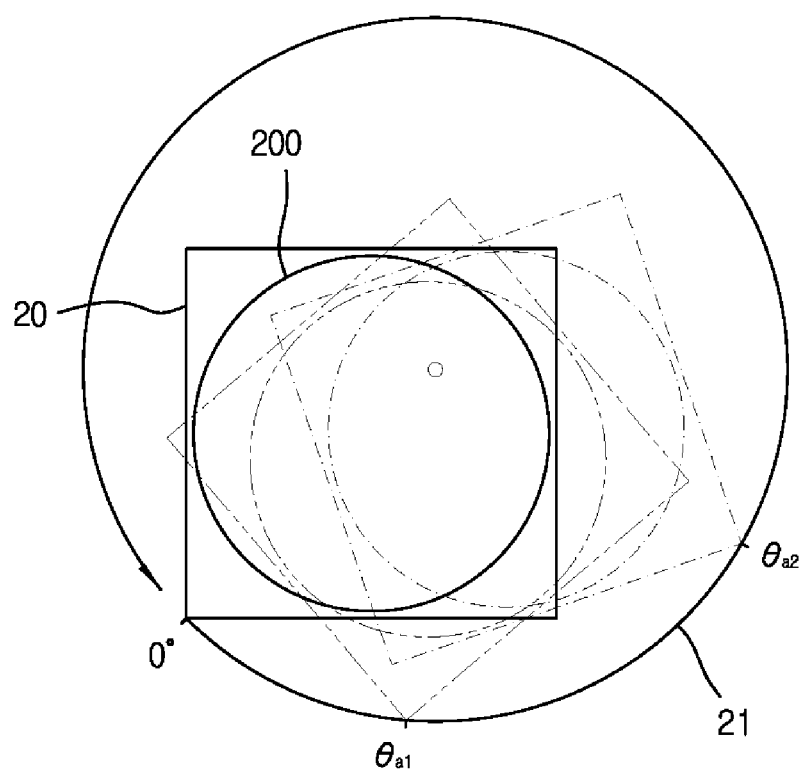
FIG. 2A is a schematic view illustrating an operational path of a stage in a semiconductor inspection device, according to one or more exemplary embodiments.
Figure 2B:
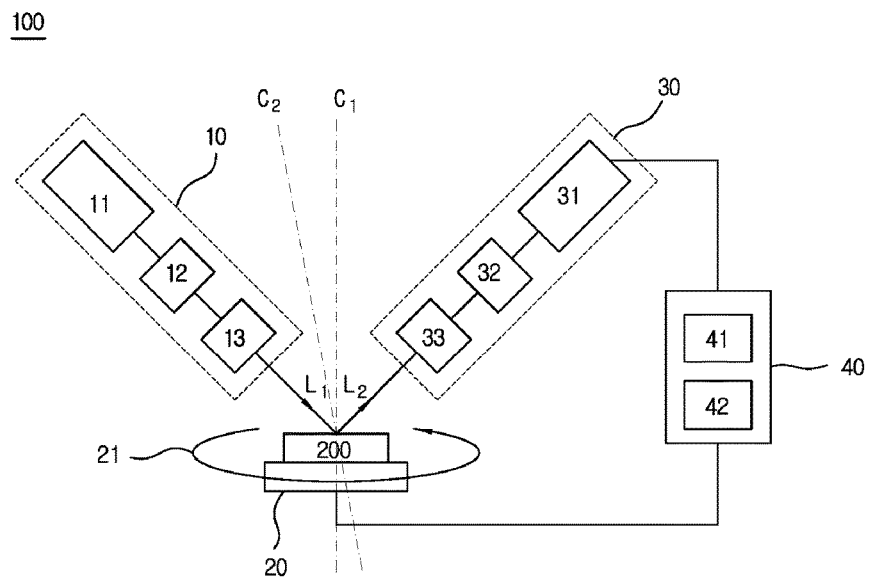
FIG. 2B is a schematic view illustrating a three dimensional operational path of a stage in a semiconductor inspection device, according to one or more exemplary embodiments.
Figure 2C:
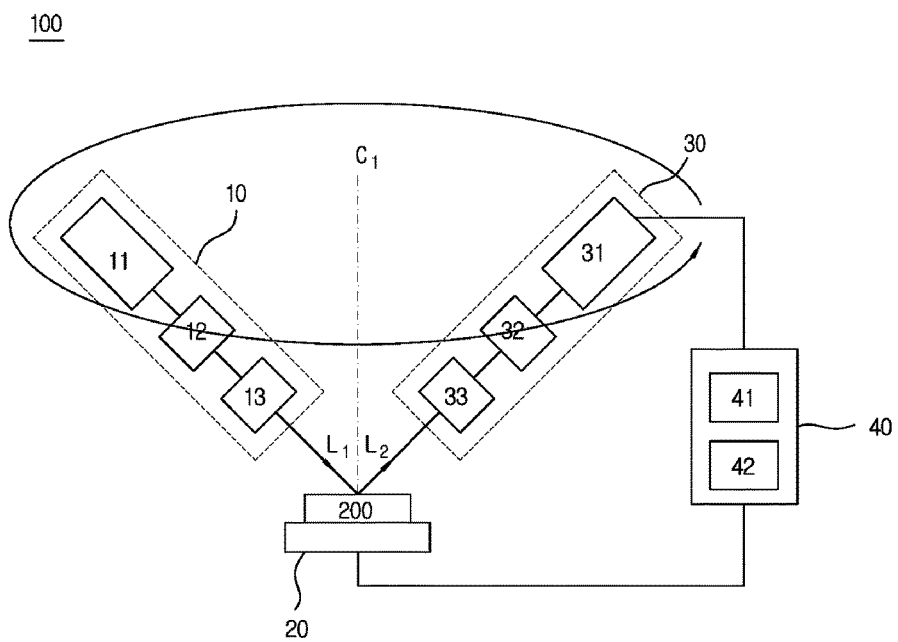
FIG. 2C is a schematic view illustrating an operational path of an emitter and a collector in a semiconductor inspection device, according to one or more exemplary embodiments.

FIG. 2A is a schematic view illustrating an operational path of a stage in a semiconductor inspection device, according to one or more exemplary embodiments. FIG. 2B is a schematic view illustrating a three dimensional operational path of a stage in a semiconductor inspection device, according to one or more exemplary embodiments. FIG. 2C is a schematic view illustrating an operational path of an emitter and a collector in a semiconductor inspection device, according to one or more exemplary embodiments.

Referring to FIG. 2A, an initial measurement of sample wafer 200 may be conducted at a reference position of 0 degrees. Once the measurement of sample wafer 200 is complete at the reference position, stage 20 may be rotated by a rotating interval of $\theta_{a1}$ to first azimuthal angle $\theta_{a1}$. In this manner, the measurement direction of sample wafer 200 incident with polarized beam $L_1$ may be changed. Once the measurement of sample wafer 200 is performed at the first azimuthal angle $\theta_{a1}$, stage 20 may be rotated by the rotating interval of $\theta_{a1}$ to second azimuthal angle $\theta_{a2}$. As such, the measurement direction of sample wafer 200 incident with polarized beam $L_1$ may be changed. The rotating angle $\theta_{a1}$ may be the same or different in each rotation, according to an inspection environment and condition. To this end, an azimuthal angle corresponding to a measurement direction of sample wafer 200 incident with polarized beam $L_1$ may be changed, according to rotating interval $\theta_{a1}$, along operational path 21 of stage 20.

According to one or more exemplary embodiments, stage 20 may rotate continuously along operational path 21, and emitter 10 may emit polarized beam $L_1$ at a point in time when stage 20 passes each rotating interval, such as the first and second azimuthal angles $\theta_{a1}$ and $\theta_{a2}$, instead of stage 20 stopping rotation at each rotating interval for measurement. The continuous rotation of stage 20 may reduce inspection time of a semiconductor pattern of sample wafer 200.

A speed of rotation of stage 20 may be controlled by controller 42. In this manner, different portions of the semiconductor pattern may be measured at different speeds with respect to one or more of the rotating intervals. For example, stage 20 may rotate at a lower speed with respect to portions of the semiconductor pattern to be more substantially inspected (e.g., to enable additional measurements to be performed with respect to polarized beam $L_1$ and reflected beam $L_2$), whereas the stage 20 may rotate at a higher speed with respect to other portions of the semiconductor pattern to be more cursorily inspected. As such, intermediary speeds may be utilized with respect to still other portions to enable a balancing between the extent of inspection and the time utilized to perform the inspection. Continuously rotating stage 20 with altering (or variable) rotational speed may reduce inspection time and increase accuracy of the inspection, as well as enable inspection resources to be devoted to those areas of the semiconductor pattern requiring more attention than other areas.

According to one or more exemplary embodiments, a rotating direction of stage 20 may alter between clockwise and counterclockwise directions. In this manner, alternately rotating stage 20 may provide measurements of a semiconductor pattern having various structural orientations.

Referring to FIG. 2B, operational path 21 of stage 20 may traverse a three dimensional path or space. For instance, a first edge of stage 20 rotating in a plane (e.g., around a first axis C1) may be shifted upwards or downwards, such that stage 20 may rotate around a second axis C2, which may be shifted from first axis C1. In other words, the pitch and/or roll of stage 20 may be modified. As such, second axis C2 may be oblique to first axis C1. In this manner, polarized beam $L_1$ may be incident to sample wafer 200 in various angles, which may enable additional inspection views of a semiconductor pattern formed on sample wafer 200, including a semiconductor pattern having a three dimensional structure, such as a vertical structure. It is noted that when the roll and/or pitch of stage 20 is modified, a position of the collector 30 may be adjusted accordingly, so as to collect reflected beam $L_2$ from shifted stage 20.

Referring to FIG. 2C, emitter 10 and collector 30 may be configured to rotate around stage 20, which may be fixed. That is, an axis of rotation of emitter 10 and collector 30 may be modified to affect the angle of incidence of polarized beam $L_1$ on a semiconductor pattern of sample wafer 200. Further, rotation of emitter 10 and collector 30 may be modified in a three dimensional space to control an angle formed between polarized beam $L_1$ and reflected beam $L_2$. In other words, the roll and pitch of emitter 10 and collector 30 may be modified to perform additional data mining on a semiconductor pattern formed on sample wafer 200.

According to one or more exemplary embodiments, emitter 10 may include two or more light sources 11, and each light source 11 may emit an optical beam having different wavelengths, waveforms, and/or intensities from each other. Each optical beam emitted from two or more light sources 11 may be incident to the same or different portions of sample wafer 200. Analyzer 32 and detector 31 may analyze and detect reflected beam $L_2$ having different wavelengths, waveforms, and/or intensities, respectively, such that sample wafer 200 may be inspected with multiple optical beams at the same or difference times to increase accuracy, or multiple semiconductor patterns formed on sample wafer 200 may be inspected in a single inspection process. To this end, light source 11 may be configured to produce illumination at various wavelengths, waveforms, and/or intensities.

Referring to back to FIG. 2A, a first interval of the rotating interval (i.e., the angle between 0 degrees and first azimuthal angle $\theta_{a1}$), and a second interval of the rotating interval (i.e., the angle between the first azimuthal angle $\theta_{a1}$ and the second azimuthal angle $\theta_{a2}$) may be the same or different from each other. For example, the rotating interval may be set to 10 degrees, such that first azimuthal angle $\theta_{a1}$ forms 10 degrees with the reference position of 0 degrees, and second azimuthal angle $\theta_{a2}$ forms 10 degrees with reference to first azimuthal angle $\theta_{a1}$. A rotational range may be divided into n rotating intervals, in which n is a rational number. The interval of azimuthal angles may be determined in consideration of a structure of a semiconductor pattern formed on sample wafer 200.

Figure 3A:
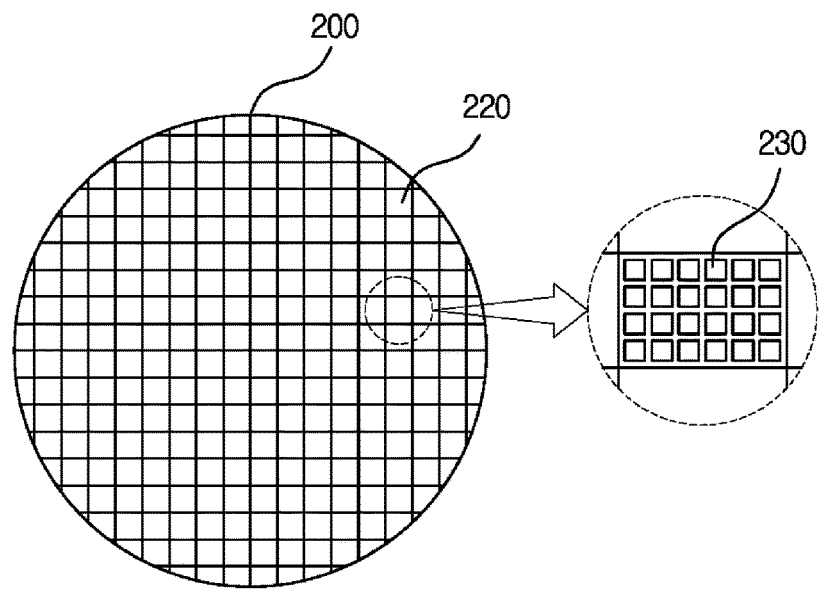
FIG. 3A is a schematic view illustrating a semiconductor pattern formed on a sample wafer, according to one or more exemplary embodiments.
Figure 3B:
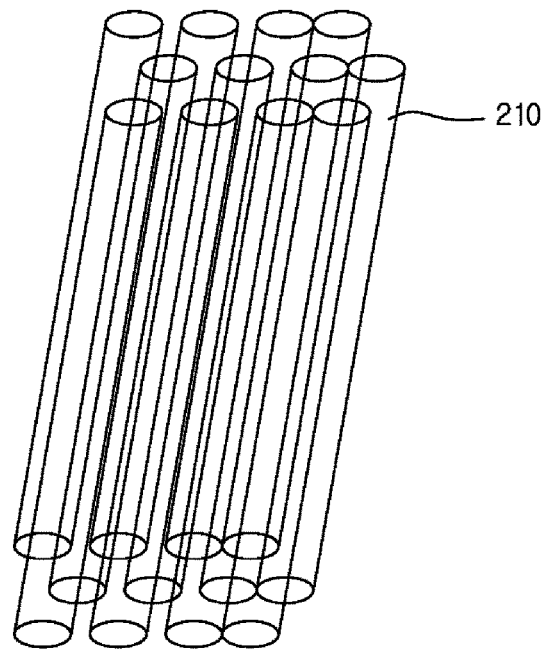
FIG. 3B is a perspective view of holes formed on the sample wafer of FIG. 3A, according to one or more exemplary embodiments.

FIG. 3A is a schematic view illustrating a semiconductor pattern formed on a sample wafer, according to one or more exemplary embodiments. FIG. 3B is a perspective view of holes formed on the sample wafer of FIG. 3A, according to one or more exemplary embodiments.

Referring to FIGS. 3A and 3B, semiconductor pattern 230 may be formed on sample wafer 200 as part of fabricating semiconductor device 220. Semiconductor pattern 230 may include holes, cells, various layers, wirings, etc. For convenience, semiconductor pattern 230 will be described in association with a pattern of holes. During the fabrication of semiconductor device 220, semiconductor pattern 230, such as holes 210, may be formed on sample wafer 200, in which holes 210 may be formed asymmetrically.

Asymmetry of semiconductor pattern 230 may be associated with the relative position of each hole 210 with respect to semiconductor pattern 230 as a whole and/or the relative structural orientation of holes 210 with respect to sample wafer 200. For instance, as seen in FIG. 3B, a distance between holes 210 in each row are different from each other. As such, holes 210 may be asymmetrical in terms of the relative position of holes 210. As used herein, asymmetry of individual semiconductor patterns 230 (e.g., holes 210) with respect to the relative position thereof will be referred to as positional asymmetry. With continued reference to FIG. 3B, holes 210 may be inclined with respect to a planar surface of sample wafer 200. In this manner, holes 210 may be asymmetrical in terms of the structural orientation of holes 210 with respect to sample wafer 200. As used herein, asymmetry of semiconductor patterns 230 with respect to the structural orientation thereof will be referred to as structural asymmetry. Hereinafter, unless stated otherwise, the asymmetry of semiconductor pattern 230 will be described with respect to the structural asymmetry of semiconductor pattern 230.

Figure 3C:
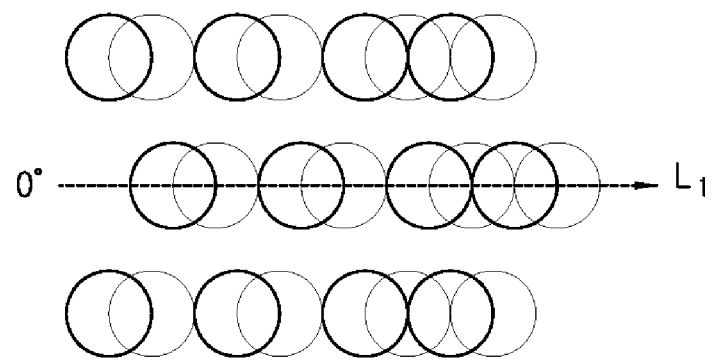
FIG. 3C is a plan view of the holes of FIG. 3B incident with a polarized beam emitted from 0 degrees with respect to a semiconductor pattern formed on the sample wafer, according to one or more exemplary embodiments.
Figure 3D:
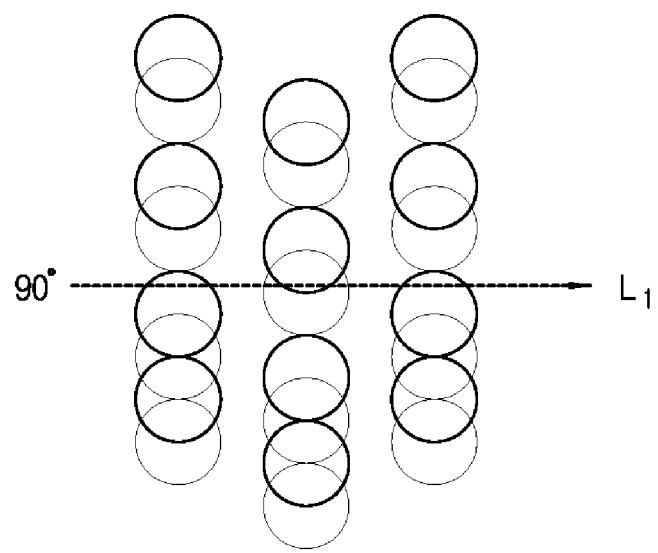
FIG. 3D is a plan view of the holes of FIG. 3B incident with a polarized beam emitted from 90 degrees with respect to a semiconductor pattern formed on the sample wafer, according to one or more exemplary embodiments.

FIG. 3C is a plan view of the holes of FIG. 3B incident with a polarized beam emitted from 0 degrees with respect to a semiconductor pattern formed on the sample wafer, according to one or more exemplary embodiments. FIG. 3D is a plan view of the holes of FIG. 3B incident with a polarized beam emitted from 90 degrees with respect to a semiconductor pattern formed on the sample wafer, according to one or more exemplary embodiments. In FIGS. 3C and 3D, an upper opening of a hole is illustrated with a darker circle and a lower opening of a hole is illustrated with a lighter circle.

Referring to FIG. 3C, to inspect the symmetry of the semiconductor pattern formed on sample wafer 200, polarized beam $L_1$ may be incident to sample wafer 200 including holes 210 from a reference position having an azimuthal angle of 0 degrees. In this manner, however, an asymmetry in sample wafer 200 may not be detected because an inclined direction of holes 210 may be the same as the direction of polarized beam $L_1$ incident thereto. As such, the inspection may determine that holes 210 are symmetrical even though an asymmetry in inclined holes 210 may exist.

As described herein, asymmetry may refer to a difference in a surface area ratio of holes 210 with respect to a direction of polarized beam $L_1$. For example, in FIG. 3C, holes 210 formed above polarized beam $L_1$ may have 1:1 surface area ratio with holes 210 formed below polarized beam $L_1$, and, thus, the asymmetry may be 0. In other words, holes 210 formed above polarized beam $L_1$ may directly overlap holes 210 formed below polarized beam $L_1$ when the image is folded in half with respect to polarized beam $L_1$. It is noted, however, that the depiction of polarized beam $L_1$ is a representation of an imaginary line bisecting the semiconductor pattern in a direction corresponding to the azimuthal angle of stage 20.

Referring to FIG. 3D, polarized beam $L_1$ may be incident to sample wafer 200 including holes 210 from a position having an azimuthal angle of 90 degrees. In this manner, an inclined direction of holes 210 formed on sample wafer 200, which may be mounted on stage 20 to form an azimuthal angle of 90 degrees with respect to the reference position, may intersect polarized beam $L_1$ incident thereto. That is, the inclined direction of holes 210 may form a 90 degree angle with polarized beam $L_1$. As such, holes 210 formed above polarized beam $L_1$ may not have a 1:1 surface area ratio with holes 210 formed below polarized beam $L_1$, and, thus, measurement data may identify the asymmetry in association with the corresponding azimuthal angle. In other words, holes 210 formed above polarized beam $L_1$ may not directly overlap holes 210 formed below polarized beam $L_1$ when the image is folded in half with respect to polarized beam $L_1$.

Although not illustrated, when polarized beam $L_1$ is incident to holes 210 formed on sample wafer 200 mounted on stage 20, which may be positioned between azimuthal angles of 0 degrees and 90 degrees, measurement data may identify the asymmetry in association with one or more corresponding azimuthal angles because an inclined direction of holes 210 may be different from a direction of polarized beam $L_1$. However, a degree of the asymmetry may be lower than when the inclined angle of holes 210 is perpendicular to the direction of polarized beam $L_1$. According to one or more exemplary embodiments, a degree of detection of the asymmetry may be the lowest when the inclined angle of a semiconductor pattern (e.g., holes 210) and a direction of polarized beam $L_1$ are the same, and a degree of detection of the asymmetry may be the greatest when the inclined angle of a semiconductor pattern perpendicularly intersects the direction of polarized beam $L_1$. As such, by measuring sample wafer 200 in various azimuthal angles, an accurate profile of a semiconductor pattern, such as an asymmetry profile of the semiconductor pattern, may be generated by comparing and analyzing various detected data at the various different azimuthal angles.

According to one or more exemplary embodiments, the types of data gathered by semiconductor inspection device 100 may include an azimuthal angle from which sample wafer 200 may be measured, an inclined angle of a semiconductor pattern, and a scalar value of at least one of first, second, third, and fourth elements of a Mueller matrix, of which may be used to quantify a degree of asymmetry of the semiconductor pattern.

Figure 4:
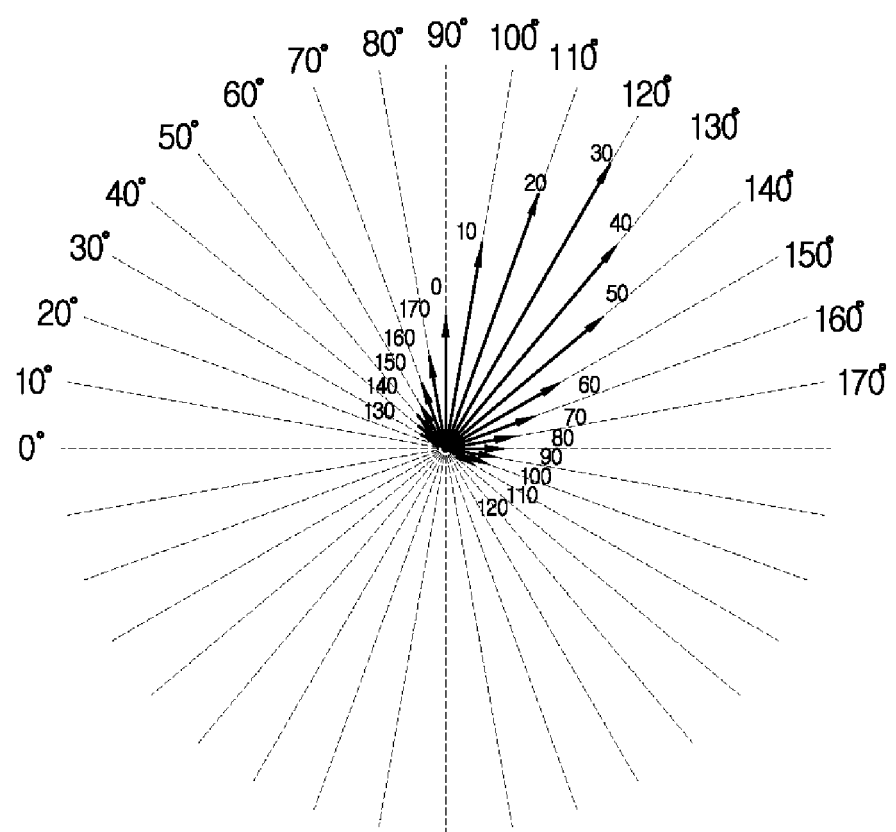
FIG. 4 is a vector diagram illustrating the asymmetry of holes, according to one or more exemplary embodiments.

FIG. 4 is a vector diagram illustrating the asymmetry of holes, according to one or more exemplary embodiments.

Referring to FIG. 4, angles indicated along a circumference may correspond to an inclined angle of a semiconductor pattern, such as holes 210, which may correspond to an asymmetry direction thereof. Inclined angles may be angles measured from 0 degrees to 170 degrees (e.g., 18 azimuthal angles). It is contemplated, however, that any suitable number of different azimuthal angles may be utilized in association with exemplary embodiments described herein. As will become more apparent below, the inclined angles plotted along the circumference may be used to approximate an actual inclined angle of a semiconductor pattern.

Each of the inclined angles plotted along the circumference may be derived by adding 90 degrees to a corresponding azimuthal angle at which sample wafer 200 is rotated and polarized beam $L_1$ is incident. In this manner, the asymmetry in a semiconductor pattern may be accurately measured because the degree of the asymmetry may be the greatest when the inclined angle of a semiconductor pattern perpendicularly intersects the direction of polarized beam $L_1$, as described above. According to exemplary embodiments, a functional relationship between the inclined angle of a semiconductor pattern and a direction of polarized beam $L_1$ may vary according to a shape and structure of a semiconductor pattern to be measured.

As seen in FIG. 4, the arrows pointing in various directions from a central point along the circumference lines may be vectors, which may be associated with a determination of the asymmetry of a semiconductor pattern with respect to an azimuthal angle of stage 20. In this manner, the direction of an arrow may correspond to an asymmetry direction (or inclined angle) of a semiconductor pattern. Each angle along the circumference lines with respect to 0 degrees to 170 degrees may correspond to a position of a semiconductor pattern at which polarized beam $L_1$ is incident (i.e., an azimuthal angle). Each angle may represent an increment of 10 degrees from 0 degrees to 170 degrees. It is noted that any suitable interval and frequency thereof may vary according to a shape and structure of a semiconductor pattern to be measured. To this end, the intervals may be constant or variable.

Referring to FIG. 4, when holes 210 have an inclined angle of 120 degrees, the asymmetry of holes 210 may be most accurately measured when polarized beam $L_1$ is incident to sample wafer 200 forming an azimuthal angle of 30 degrees, thus perpendicularly intersecting the direction of polarized beam $L_1$ among the other azimuthal angles. As such, the vector at 30 degrees, corresponding to a measurement associated with polarized beam $L_1$ incident to sample wafer 200 forming an azimuthal angle of 30 degrees, may indicate the greatest degree of asymmetry, as illustrated by a length of the vector at 30 degrees. The vector at 120 degrees, corresponding to a measurement associated with polarized beam $L_1$ incident to sample wafer 200 forming an azimuthal angle of 120 degrees, may indicate the lowest degree of asymmetry, as illustrated by a length of the vector at 120 degrees. In other words, the direction of polarized beam $L_1$ at 30 degrees may be the same direction as the inclined angle of holes 210 at 120 degrees. The scalar value, which may correspond to a size of arrows, illustrated as a vector, may be a sum of at least one or more of the first, second, third, and fourth components of a generated Mueller matrix associated with an asymmetry of a semiconductor pattern. Accordingly, as the arrow at 30 degrees, among the other arrows, has the greatest length among arrows illustrated in a vector diagram of FIG. 4, semiconductor inspection device 100 may determine that holes 210 have an inclined angle of 120 degrees.

As illustrated in FIG. 4, based on the 18 data points associated with a degree of asymmetry (i.e., Mueller matrix components) of a semiconductor pattern and a direction (i.e., inclined angle) thereof measured between 0 to 170 azimuthal angles, a profile of a semiconductor pattern that may include asymmetry information may be generated. The generated profile may be fed back to a semiconductor fabrication process, so as to improve production yield and electrical properties of a semiconductor device. It is noted that the number of data measured and a range and interval of azimuthal angles may vary according to a shape and structure of a semiconductor pattern to be measured.

Although not illustrated, information associated with relative positions (or mapping information) of semiconductor pattern 230 formed on sample wafer 200 may be stored in a database. Semiconductor inspection device 100 may retrieve the mapping information to identify a positional asymmetry of semiconductor pattern 230. For example, when holes 210 are structurally symmetrical, but have a positional asymmetry (e.g., the lighter circle overlaps the darker circle for each holes in FIG. 3D), processor 40 may compare the retrieved mapping information to each measurement associated with polarized beam $L_1$ incident to sample wafer 200. In this manner, semiconductor inspection device 100 may offset positional asymmetry elements from the measurements, and determine that holes 210 are symmetrical (or structurally symmetrical).

Figure 5:
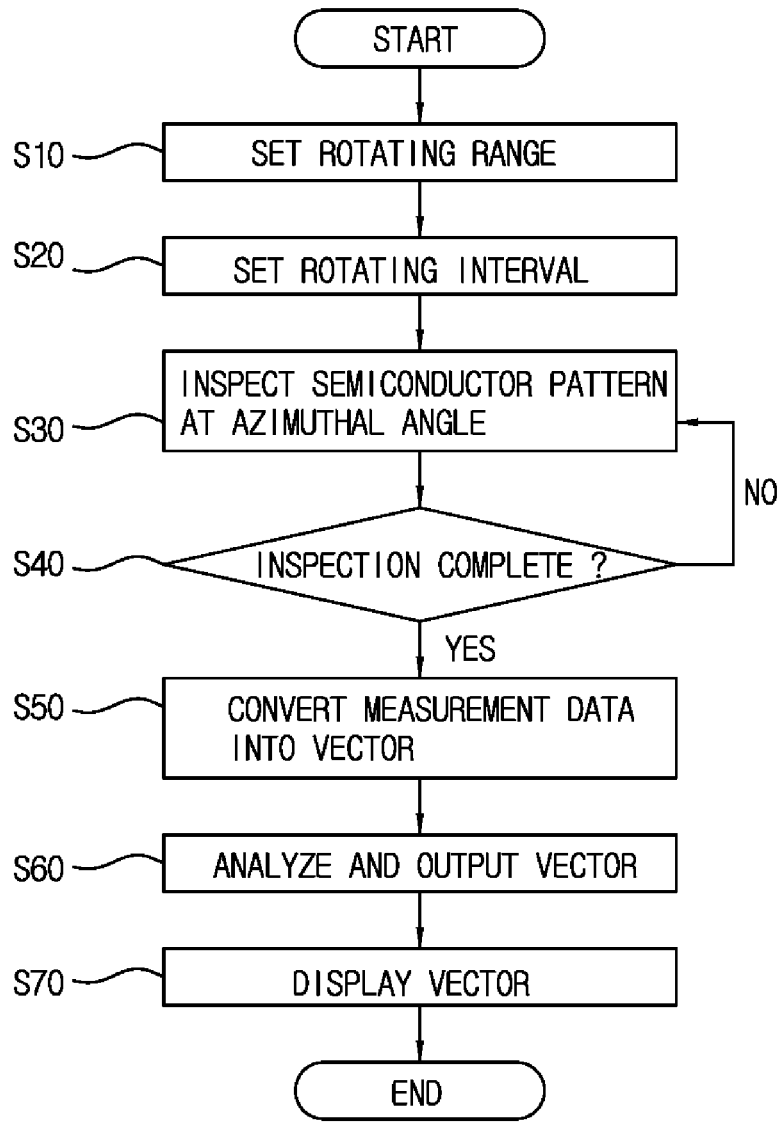
FIG. 5 is a flowchart of a process to inspect a semiconductor pattern of a sample wafer, according to one or more exemplary embodiments.

FIG. 5 is a flowchart of a process to inspect a semiconductor pattern of a sample wafer, according to exemplary embodiments.

Referring to FIG. 5, a rotating range of stage 20, on which sample wafer 200 may be mounted, may be set from 0 degrees to a desired azimuthal angle in step S10. For example, a rotating range of stage 20 illustrated with reference to FIG. 4 may be set from 0 degrees to 170 degrees. The rotating range of stage 20 in step S10 may be varied according to a shape and structure of a semiconductor pattern formed on sample wafer 200.

In step S20, a rotating interval of stage 20 within the rotating range may be set. The rotating interval may be set to be uniform across the rotating range or be different from each other or at least one other interval. For example, a rotating interval of stage 20 illustrated with reference to FIG. 4 may be uniformly set to 10 degrees across the rotating range of 0 degrees to 170 degrees. It is noted that setting a rotating interval of stage 20 (S20) may be performed prior to setting a rotating range of stage 20 (S10).

In step S30, stage 20 may rotate by the rotating interval within the rotating range determined at S10 and S20. That is, sample wafer 200 mounted on stage 20 may sequentially rotate from a reference position by the rotating interval, such that a semiconductor pattern of sample wafer 200 may be inspected at each azimuthal angle corresponding to the rotating interval, so as to measure an asymmetry of the semiconductor pattern, such as holes 210.

In step S40, operator 41 of processor 40 may determine whether sample wafer 200 has been inspected at each rotating intervals within the rotating range, by receiving a signal that may be transmitted when a measurement from one azimuthal angle has been completed. If another inspection is to be performed, operator 41 and/or controller 42 may control stage 20 and one or more components of inspection device 100 to continue inspection of sample wafer 200.

In step S50, measurement data obtained from measuring sample wafer 200 at each determined azimuthal angle may be processed and converted into a vector, such as illustrated in association with FIG. 4. A vector magnitude may be illustrated as a sum of at least one or more of the first, second, third, and fourth components of a generated Mueller matrix, which may represent a degree of asymmetry of a semiconductor pattern. Operator 41 and controller 42 may utilize one or more of the first, second, third, and fourth components of Mueller matrix as an output for representing a degree of asymmetry of a semiconductor pattern. As such, multiple vectors may be processed with respect to the determined azimuthal angles, as illustrated with reference to FIG. 4.

In step S60, calculated vector values may be analyzed and output by processor 40, which may include a minimum vector magnitude, a maximum vector magnitude, and an average vector magnitude. For example, in FIG. 4, a magnitude of a vector (e.g., the arrow at 30 degrees) corresponding to an inclined angle of 120 degrees may be the greatest. As such, semiconductor inspection device 100 may determine that a semiconductor pattern may be inclined at 120 degrees. To this end, an accurate profile of a semiconductor pattern formed on sample wafer 200 may be obtained by measuring sample wafer 200 from various azimuthal angles, even without information associated with asymmetry of the semiconductor pattern itself.

In step S70, the magnitude of vectors processed by operator 41 and controller 42 may be displayed on a display that may be included in processor 40.

According to exemplary embodiments, semiconductor inspection device 100 may measure a semiconductor pattern formed on sample wafer 200 from various azimuthal angles, such that an accurate profile of the semiconductor pattern may be obtained without information associated with asymmetry of the semiconductor pattern.

Although certain exemplary embodiments and implementations have been described herein, other embodiments and modifications will be apparent from this description. Accordingly, the inventive concept is not limited to such exemplary embodiments, but rather to the broader scope of the presented claims and various obvious modifications and equivalent arrangements.

What is claimed is:

1. An ellipsometer, comprising:
   a stage configured to support a substrate comprising a pattern;
   a light source configured to emit illumination toward the substrate;
   a polarizer configured to polarize the illumination;
   a detector configured to generate, in association with a plurality of azimuthal angles, data corresponding to polarized illumination reflected from the substrate; and
   a processor configured to:
      control rotation of the stage in association with sequential inspection of the pattern at the plurality of azimuthal angles; and
      determine asymmetry of the pattern based on the data,
   wherein each azimuthal angle of the plurality of azimuthal angles corresponds to a different rotational state of the stage.

2. The ellipsometer of claim 1, wherein:
   the processor is configured to generate a plurality of vectors respectively corresponding to the plurality of azimuthal angles; and
   each vector of the plurality of vectors comprises:
      a magnitude determined based on the data; and
      a direction corresponding to a rotational state of the stage.

3. The ellipsometer of claim 2, wherein the processor is configured to determine the asymmetry based on a comparison of the plurality of vectors.

4. The ellipsometer of claim 3, wherein:
   a degree of the asymmetry corresponds to a vector with a greatest magnitude; and
   a direction of the asymmetry corresponds to a sum of a rotational state of the stage associated with the vector and 90 degrees.

5. The ellipsometer of claim 1, wherein the data corresponds to components of a Mueller matrix.

6. The ellipsometer of claim 1, wherein the plurality of azimuthal angles range from greater than or equal to 0 degrees to less than or equal to 180 degrees.

7. The ellipsometer of claim 1, wherein the range is divided into n rotational intervals, n being a rational number.

8. The ellipsometer of claim 1, further comprising:
   a first compensator configured to modify a polarization state of the polarized illumination propagating towards the substrate from the polarizer; and
   a second compensator configured to modify a polarization state of the polarized illumination reflected from the substrate towards the detector,
   wherein the detector comprises:
      an analyzer configured to determine orthogonal components of the polarized illumination reflected from the substrate; and
      a sensor configured to determine a quantity of the polarized illumination propagating through the analyzer.

9. The ellipsometer of claim 1, wherein the processor is configured to:
   control the stage to rotate through the plurality of azimuthal angles with a continuous motion; and
   actuate the light source and the detector in association with each azimuthal angle of the plurality of azimuthal angles.

10. The ellipsometer of claim 1, wherein the light source is configured to emit other illumination, wavelengths of the other illumination and the illumination are different from one another.

11. The ellipsometer of claim 1, wherein the stage is configured to rotate about a plurality of axes of rotation.

12. The ellipsometer of claim 1, wherein an at least partially formed semiconductor device comprises the pattern.

* * * * *